US005158942A

United States Patent [19]

Herrmann et al.

[11] Patent Number: 5,158,942

[45] Date of Patent: Oct. 27, 1992

[54] PROCESS OF USING PHOSPHOLIPID DERIVATIVES TO INHIBIT MULTIPLICATION OF THE HUMAN IMMUNODEFICIENCY VIRUS

[75] Inventors: Dieter Herrmann, Heidelberg; Elmar Bosies, Weinheim; Harald Zilch, Mannheim; Edith Koch, Penzburg, all of Fed. Rep. of Germany

[73] Assignee: Boehringer Mannheim GmbH, Mannheim, Fed. Rep. of Germany

[21] Appl. No.: 572,475

[22] Filed: Aug. 23, 1990

[30] Foreign Application Priority Data

Sep. 2, 1989 [DE] Fed. Rep. of Germany ....... 3929217

[51] Int. Cl.$^5$ ....................... C07F 9/10; A61K 31/685

[52] U.S. Cl. ..................................... 514/77; 514/114; 558/169

[58] Field of Search ................... 558/169; 514/114, 77

[56] References Cited

U.S. PATENT DOCUMENTS 4,444,766 4/1984 Bosies et al. .......................... 514/77

FOREIGN PATENT DOCUMENTS 316117 5/1989 European Pat. Off. .

3638126 5/1988 Fed. Rep. of Germany ...... 558/169

182365 1/1989 Japan .

OTHER PUBLICATIONS

Sandow et al., Pharmazie 41: 404–406 (1986).

Nali et al., Gazz. Chim. Ital, 116: 25–27 (1986).

*Primary Examiner*—Robert W. Ramsuer

*Assistant Examiner*—Michael G. Ambrose

*Attorney, Agent, or Firm*—Felfe & Lynch

[57] ABSTRACT

The present invention is concerned with the use of compounds of the general formula:

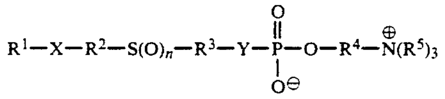

(I)

and of the pharmacologically acceptable salts thereof, as well as of the optical isomers thereof for the preparation of pharmaceutical compositions with antiviral action.

The present invention also provides new phospholipid derivatives.

8 Claims, No Drawings

PROCESS OF USING PHOSPHOLIPID DERIVATIVES TO INHIBIT MULTIPLICATION OF THE HUMAN IMMUNODEFICIENCY VIRUS

The present invention is concerned with the new use of phospholipid derivatives, some of which are new, processes for the preparation thereof and pharmaceutical compositions containing them.

The present invention is concerned with the use of compounds of the general formula:

$$R^1-X-R^2-S(O)_n-R^3-Y-\underset{O^\ominus}{\overset{O}{\overset{\|}{P}}}-O-R^4-\overset{\oplus}{N}(R^5)_3 \qquad (I)$$

wherein X is a valency bond, an oxygen or sulphur atom, a sulphinyl, sulphonyl, aminocarbonyl, carbonylamino or ureido (—NH—CO—NH—) group or a $C_3$–$C_8$-cycloalkylene or phenylene radical, Y is an oxygen or sulphur atom, $R^1$ is a hydrogen atom or a straight-chained or branched, saturated or unsaturated alkyl radical containing up to 18 carbon atoms which can be substituted one or more times by phenyl, halogen, $C_1$–$C_4$-alkoxy, $C_1$–$C_4$-alkylmercapto, $C_1$–$C_4$-alkoxycarbonyl, $C_1$–$C_4$-alkanesulphinyl or $C_1$–$C_4$-alkanesulphonyl, $R^2$ is a straight-chained or branched, saturated or unsaturated alkylene chain containing up to 18 carbon atoms which can be substituted one or more times by halogen, phenyl, $C_1$–$C_4$-alkoxy, $C_1$–$C_4$-alkoxycarbonyl, $C_1$–$C_4$-alkylmercapto, $C_1$–$C_4$-alkanesulphinyl or $C_1$–$C_4$-alkanesulphonyl, $R^3$ is a straight-chained or branched, saturated or unsaturated alkylene chain containing 2 to 8 carbon atoms in which one methylene moiety can be replaced by a $C_5$–$C_7$-cycloalkane ring and can be substituted one or more times by hydroxyl, halogen, nitrile, $C_5$–$C_7$-cycloalkyl, phenyl, $C_1$–$C_{20}$-alkoxycarbonyl, $C_1$–$C_{20}$-alkylcarbamoyl, $C_1$–$C_{20}$-alkylmercapto, $C_1$–$C_{20}$-alkanesulphinyl, $C_1$–$C_{20}$-alkanesulphonyl or $C_1$–$C_{20}$-acylamino or by $C_1$–$C_{20}$-alkoxy which, in turn, can be substituted by phenyl, $C_1$–$C_{20}$-alkylmercapto, $C_1$–$C_{20}$-alkanesulphinyl, $C_1$–$C_{20}$-alkanesulphonyl, $C_1$–$C_{20}$-acylamino, $C_1$–$C_{20}$-alkoxycarbonyl, nitrile, hydroxyl, $C_1$–$C_{20}$-alkoxy or $C_1$–$C_{20}$-alkylcarbamoyl, $R^4$ is a straight-chained or branched alkylene chain containing 2 to 4 carbon atoms, $R^5$ is a hydrogen atom or a $C_1$–$C_6$-alkyl radical and the three substituents $R^5$ on the nitrogen atom can be the same or different and n is 0, 1 or 2; of the pharmacologically acceptable salts thereof, as well as of the optical isomers thereof for the preparation of pharmaceutical compositions with antiviral action.

In U.S. Pat. No. 4,444,766 there are described sulphur-containing phospholipids with the above-given structure, as well as the use thereof for the preparation of pharmaceutical compositions. However, this Patent exclusively describes the cancerostatic action of these phospholipids which are especially suitable for the preparation of anti-tumour agents.

The compound 3-hexadecylmercapto-2-hexadecyloxypropyl-1-phosphoric acid monocholine ester with potential immune-stimulating action is already known from the literature (see Gazz. Chim. Ital., 116, 25/1986).

Surprisingly, we have now found that these phospholipids display an outstanding antiviral action and are, therefore, especially well suited for the treatment of viral and retroviral infections. Viral infections of mammals and especially of humans are widespread. In spite of intensive efforts, it has hitherto not been possible to provide chemotherapeutics which interfere with recognisable substantial success, causally or symptomatically, with the pathological occurrences caused virally or retrovirally. At present, it is not possible to cure certain viral diseases, for example the acquired immune deficiency syndrome (AIDS), the AIDS-related complex (ARC) and the preliminary stages thereof, herpes, cytomegalovirus (CMV), influenza and other viral infections or favourably to influence the symptoms thereof chemotherapeutically. At present, for example, for the treatment of AIDS, the compound 3'-azido-3'deoxythymidine (AZT), which is also known as zidovudine and Retrovir ® is just about the only antiviral available. However, AZT is characterized by a very narrow therapeutic breadth and by very severe toxicities occurring even in the therapeutic range (see M. S. Hirsch, J. Infect.Dis., 157, 427–431/1988).

Therefore, there is a great need for chemotherapeutics which interfere as specifically as possible with diseases caused by viruses and retroviruses or with the symptoms thereof without, however, influencing the other normally occurring natural body functions.

Therefore, it is an object of the present invention to provide antivirally-effective agents and new phospholipid derivatives.

This object is achieved by the use of the phospholipids of general formula (I).

The phospholipids of general formula (I) inhibit very specifically the multiplication of viruses, including the following viruses: HIV, herpes, Sendai, cytomegalovirus (CMV), influenza, parainfluenza, Epstein-Barr (EBV), vesicular stomatitis virus (VSV), hepatitis, meningitis, encephalitis and the like. The above-mentioned compounds can advantageously be used prophylactically or therapeutically in the case of the treatment of all diseases in which a viral or retroviral infection is of pathophysiological, symptomatic or clinical relevance.

In the phospholipids of general formula (I), an alkyl radical in the substituent $R^5$ is a hydrocarbon radical containing up to 6 carbon atoms and especially a methyl or ethyl radical.

The alkyl moieties of the substituents mentioned in the definitions of $R^1$-$R^3$, for example alkyl, alkoxycarbonyl, alkylmercapto, alkanesulphinyl and alkanesulphonyl radicals, mean, in all cases, radicals with a chain length of 1 to 20 carbon atoms. There are especially preferred those radicals with a chain length of at least 8 and preferably of 10 carbon atoms and at most of up to 18 and preferably of up to 16 or 15 carbon atoms, for example alkyl moieties with 8 to 18, especially 8 to 16, 8 to 15, 10 to 16 or 10 to 15 carbon atoms. As examples thereof, there may be mentioned octadecylmercapto, tetradecyloxy and octylmercapto radicals. A $C_1$–$C_{20}$-acylamino radical is especially preferably a $C_1$–$C_{20}$-alkylcarbonylamino radical.

The cycloalkylene radicals of the substituent X are radicals containing 3 to 8 carbon atoms and especially cyclopropylene, cyclopentylene and cyclohexylene radicals.

Cycloalkane rings which can also be components of the alkylene chain of the substituent $R^3$ are the cyclopentane, cyclohexane and cycloheptane rings, in which the rings can also be substituted by $C_1$–$C_6$-alkyl radicals. In this sense, $R^3$ can be, for example, a $C_1$–$C_4$- alkyl-$C_3$–$C_8$-cycloalkylene or $C_3$–$C_8$-cycloalkyl-$C_1$–$C_4$-alkylene radical.

Halogen means fluorine, chlorine, bromine or iodine but preferably fluorine.

When X is a valency bond, the radical $R^1$—X—$R^2$— is an alkyl radical containing up to 20 carbon atoms, which can be straight-chained or branched, saturated or unsaturated. Preferred straight-chained radicals include the eicosyl, octadecyl, heptadecyl, hexadecyl, tetradecyl, dodecyl and octyl radicals.

In the definitions of $R^1$–$R^3$, an unsaturated alkyl radical is to be understood to be especially an alkyl radical which contains up to four double bonds but preferably one or two double bonds.

The substituent $R^3$ is preferably a —$CH_2$—$CH_2$—$CH_2$— radical, the middle methylene moiety of which can be substituted once or twice by alkyl, alkoxy, alkylmercapto, alkanesulphinyl, alkanesulphonyl, alkoxyalkylene, benzyloxy, hydroxyl or halogen and can possibly be substituted on carbon atoms $C^1$–$C^3$ by alkyl radicals which can also form a ring.

Preferred compounds of general formula (I) are especially derivatives of propan-1-ol-, propan-2-ol-and propane-1-thiol-phosphoric acid monocholine esters, in which the 3-position of the propanol is substituted by an alkylmercapto, alkanesulphinyl or alkanesulphonyl radical and is possibly also substituted in the 1- or 2-position.

The present invention also provides new compounds which display especially good antiviral action, defined by the general formula:

$$R^1—X—R^2—S(O)_n—CH_2—A—Y—\overset{\overset{\displaystyle O}{\|}}{\underset{\underset{\displaystyle O^\ominus}{|}}{P}}—O—R^4—\overset{\oplus}{N}(R^5)_3 \quad (II)$$

wherein A is a —CH(Z)—$CH_2$— or —CH($CH_2$—Z)— radical and Z is a $C_1$–$C_{20}$-alkoxycarbonyl, $C_1$–$C_{20}$-alkylaminocarbonyl, $C_1$–$C_{20}$-alkylmercapto, $C_1$–$C_{20}$-alkanesulphinyl, $C_1$–$C_{20}$-alkanesulphonyl, $C_1$–$C_{20}$-alkylcarbonylamino or $C_1$–$C_{20}$-alkoxy radical and the other symbols $R^1$, X, $R^2$, n, Y, $R^4$ and $R^5$ have substantially the above-given meanings. The alkyl moieties of the above-mentioned radicals preferably have a chain length of at least 8 and most preferably of at least 10 carbon atoms and at most up to 18 and preferably up to 16 or 15 carbon atoms.

In general formulae (I) and (II), those phospholipids display an especially good antiviral action when they are characterised by the following features: $R^1$ is preferably a straight-chained $C_5$–$C_{15}$-alkyl radical which can be substituted by a $C_1$–$C_6$-alkoxy radical, $R^1$ preferably being a pentyl, hexyl, decyl, tridecyl or pentadecyl radical. As $C_1$–$C_6$-alkoxy substituent, the n-butyloxy radical is preferred. If X is a valency bond, $R^1$ is preferably a hydrogen atom. X is preferably a valency bond or an oxygen or sulphur atom but is especially preferred as a valency bond. $R^2$ is preferably a straight-chained $C_2$–$C_{18}$-alkylene radical and especially a $C_8$–$C_{16}$-, $C_8$–$C_{15}$- or $C_{10}$–$C_{15}$-alkylene radical, for example an octylene, decylene, undecylene, dodecylene, tridecylene, tetradecylene, pentadecylene, hexadecylene or heptadecylene radical, the decylene, undecylene, dodecylene, tridecylene and tetradecylene radicals being especially preferred.

In general formula (I), $R^3$ is preferably a straight-chained $C_2$–$C_6$-alkylene radical and is especially preferred as a propylene radical which can be substituted by a hydroxyl, $C_1$–$C_{20}$-alkylmercapto, $C_1$–$C_{20}$-alkanesulphinyl, $C_1$–$C_{20}$-alkanesulphonyl, $C_1$–$C_{20}$-alkoxy, $C_1$–$C_{20}$-alkoxycarbonyl or $C_1$–$C_{20}$-alkylaminocarbonyl radical, in which the previously mentioned $C_1$–$C_{20}$-alkyl moieties preferably contain 8 to 16 and especially 10 to 15 carbon atoms. If $R^3$ represents a propylene radical, the previously mentioned substituents can be in the 1- or 2-position of the propylene radical, in which case the $R^1$—X—$R^2$—$S(O)_n$— radical is to be designated as being in the 3-position and the —Y—$P(O_2)$O—$R^4$—$N(R^5)_3$ radical must then be in the 2- or 1-position, depending upon the above-mentioned substituents.

In this sense, as substituents of the group $R^3$, the following radicals are preferred: $C_8$–$C_{16}$-alkoxy, for example octyloxy, decyloxy, undecyloxy, dodecyloxy and hexadecyloxy; $C_{10}$–$C_{16}$-alkylmercapto, for example decylmercapto and undecylmercapto; as well as $C_{10}$–$C_{15}$-alkoxycarbonyl, for example decyloxycarbonyl; $C_{10}$–$C_{15}$-alkylaminocarbonyl, for example decylaminocarbonyl; and $C_{10}$–$C_{15}$-alkylcarbonylamino, for example decylcarbonylamino.

In general formula (II), Z is preferably a hydroxyl, $C_1$–$C_{20}$-alkylmercapto, $C_1$–$C_{20}$-alkanesulphinyl, $C_1$–$C_{20}$-alkanesulphonyl, $C_1$–$C_{20}$-alkoxy, $C_1$–$C_{20}$-alkoxycarbonyl, $C_1$–$C_{20}$-alkylaminocarbonyl or $C_1$–$C_{20}$-alkylcarbonylamino radical, in which the alkyl moieties preferably contain 8 to 16 and especially 10 to 15 carbon atoms.

$R^4$ is especially preferably a straight-chained or branched $C_2$–$C_4$-alkylene radical, the ethylene radical being preferred.

$R^5$ is especially a hydrogen atom or a $C_1$–$C_4$-alkyl radical, the methyl radical being preferred.

By the definition of the $-N^{\oplus}(R^5)_3$ radical in compounds of general formulae (I) and (II) are to be understood not only the identically substituted nitrogen derivatives, for example the trimethylammonium radical, but also the mixed substituted derivatives, for example dimethylammonium, diethylammonium, n-butyldimethylammonium and methyl-diethylammonium radicals, as well as all variants possible by the combinations of the radicals given in the definition of $R^5$.

Especially preferred compounds of general formula (II) are those in which the $R^1$—X—$R^2$— radical is a $C_8$–$C_{16}$-alkyl radical, for example an octyl, decyl, undecyl, dodecyl, tridecyl, pentadecyl or hexadecyl radical and Z is a $C_{10}$–$C_{15}$-alkylmercapto, $C_{10}$–$C_{15}$-alkoxy, $C_{10}$–$C_{15}$-alkoxycarbonyl, $C_{10}$–$C_{15}$-alkylaminocarbonyl or $C_{10}$–$C_{15}$-alkylcarbonylamino radical, for example a decylmercapto, undecylmercapto, decyloxy, undecyloxy, dodecyloxy, decyloxycarbonyl, decylaminocarbonyl or decylcarbonylamino radical.

The compounds of general formulae (I) and (II) can be prepared by the processes described in U.S. Pat. No. 4,444,766.

However, for the preparation of compounds of general formulae (I) and (II), the following process is preferred:

A compound of the general formula:

$$R^1—X—R^2—S(O)_n—R^3—YH \quad (III)$$

wherein $R^1$, $R^2$, $R^3$, X, Y and n have the above-given meanings, is reacted with a compound of the general formula:

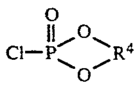

(IV)

in which $R^4$ has the above-given meaning, in the presence of an acid-binding agent and the reaction product is treated directly with an optionally alkylated ammonia.

The compounds of general formula (III) can be prepared analogously to the disclosures in Lipids, 22, 947/1987 and to the further literature cited therein. Compounds of general formula (IV) are commercially available.

As a rule, the process is carried out in such a manner that an alkanol or alkanethiol of general formula (III) is reacted with a compound of general formula (IV) in the presence of an acid-binding agent, for example triethylamine, in an anhydrous inert organic solvent, for example a chlorinated hydrocarbon or toluene, at a temperature from about the freezing point to ambient temperature and the reaction product is treated directly with a possibly alkylated ammonia. For this purpose, the ammonia or alkylamine is dissolved in a medium which sufficiently well dissolves not only the phosphoric acid diester but also ammonia or the amine, for which purpose mixtures of acetonitrile or lower alcohols with chlorinated hydrocarbons are especially suitable, and the reaction is completed at a temperature of from 20° to 70° C.

It is also possible to proceed stepwise, i.e. an alkylammonium radical is first introduced, followed by reaction with an alkyl halide to give a di- or trialkylammonium alkyl ester.

All intermediate stages as well as end products can be easily purified by column chromatography on silica gel with conventional elution agents, for example diethyl ether, ligroin, chlorinated hydrocarbons, lower alcohols and mixtures thereof. In the case of betaine-like end products, it is preferable to add some water.

The compounds of general formulae (I) and (II) can also be subsequently converted into other compounds of general formulaes (I) and (II), for example by oxidation of compounds in which n is 0 to give compounds in which n is 1 or 2.

The pharmacologically acceptable salts are obtained in the usual way, for example by neutralisation of the compounds of general formula (I) with non-toxic inorganic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

Pharmaceutical compositions containing compounds of the general formula (I) or (II) for the treatment of viral infections can be administered enterally or parenterally in liquid or solid form. For this purpose, there can be used the conventional forms of administration, for example tablets, capsules, dragees, syrups, solutions and suspensions. As injection medium, it is preferred to use water which contains the additives usual in the case of injection solutions, for example stabilising agents, solubilising agents and/or buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carriers for injection solutions must be sterile and are preferably placed in ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats, solid high molecular weight polymers (such as polyethylene glycol) and the like. Compositions suitable for oral administration can, if desired, contain flavouring and/or sweetening agents.

The dosage can depend upon various factors, such as the mode of administration, species, age and individual state of health. The compounds according to the present invention are usually administered in amounts of from 0.1 to 100 mg., preferably of from 0.2 to 80 mg. per day and per kg. of body weight. It is preferred to divide up the daily dosage into 2 to 5 administrations, in which case with each administration 1 or 2 tablets with a content of active material of 0.5 to 500 mg. is given. The tablets can also be retarded, in which case the number of administrations per day can be reduced to 1 to 3. The active material content of the retarded tablets can be from 2 to 1000 mg. The active material can also be given by continuous infusion, in which case amounts of from 5 to 1000 mg. per day normally suffice.

In the meaning of the present invention, there come into question, apart from the compounds mentioned in the following Examples and the compounds derived by the combination of all meanings of the substituents given in the claims, also the following compounds of general formula (I):

1. 3-dodecylmercaptopropyl-1-phosphoric acid monocholine ester
2. 3-dodecylsulphonylpropyl-1-phosphoric acid monocholine ester
3. 3-(2-pentadecyloxyethylmercapto)-propyl-1-phosphoric acid monocholine ester
4. 3-(2-pentadecyloxyethylsulphonyl)-propyl-1-phosphoric acid monocholine ester
5. 3-(2-pentadecylmercaptoethylmercapto)-propyl-1-phosphoric acid monocholine ester
6. 3-(2-pentadecylsulphonylethylmercapto)-propyl-1-phosphoric acid monocholine ester
7. 3-tetradecylmercaptopropyl-1-phosphoric acid monocholine ester
8. 3-(4-tridecyloxybutylmercapto)-propyl-1-phosphoric acid monocholine ester
9. 3-pentadecylmercaptopropyl-1-phosphoric acid monocholine ester
10. 3-(10-n-butoxydecyloxyethylmercapto)-propyl-1-phosphoric acid monocholine ester
11. 3-(11-hexyloxyundecylmercapto)-propyl-1-phosphoric acid monocholine ester
12. 3-(7-decyloxyheptylmercapto)-propyl-1-phosporic acid monocholine ester
13. thiophosphoric acid-O-choline ester-S-3-heptadecylmercaptopropyl ester.

Furthermore, the following compounds of general formula (II) are also to be mentioned:

1. 3-dodecylmercapto-2-decylmercaptopropyl-1-phosphoric acid monocholine ester
2. dodecylmercapto-2-decyloxycarbonylpropyl-1-phosphoric acid monocholine ester
3. 3-dodecylmercapto-2-decylaminocarbonylpropyl-1-phosphoric acid monocholine ester
4. 3-(12-pentyloxydodecylmercapto)-2-decyloxypropyl-1-phosphoric acid monocholine ester 5. 3-undecylsulphonyl-2-undecyloxypropyl-1-phosphoric acid monocholine ester
6. 3-tridecylsulphinyl-2-undecyloxypropyl-1-phosphoric acid monocholine ester
7. 3-tridecylsulphonyl-2-undecyloxypropyl-1-phosphoric acid monocholine ester
8. 3-tetradecylsulphonyl-2-undecyloxypropyl-1-phosphoric acid monocholine ester
9. 3-tridecylmercapto-2-decylmercaptopropyl-1-phosphoric acid monocholine ester
10. 3-tetradecylmercapto-2-decylmercaptopropyl-1-phosphoric acid monocholine ester
11. 3-decylmercapto-1-dodecyloxypropyl-2-phosphoric acid monocholine ester
12. 3-dodecylmercapto-1-decyloxypropyl-2-phosphoric acid monocholine ester
13. 1,3-bis-(undecylmercapto)-propyl-2-phosphoric acid monocholine ester.

The following Examples are given for the purpose of illustrating the present invention:

EXAMPLE 1

3-Dodecylmercapto-2-decyloxypropyl-1-phosphoric acid monocholine ester 4.4 g. 3-Dodecylmercapto-2-decyloxypropan-1-ol in 30 ml. dichloromethane as well as 4.1 ml. triethylamine are mixed at −25° C. with a solution of 2.6 g. 2-chloro-2-oxo-1,3,2-dioxyphospholane (Fluka) in 10 ml. dichloromethane and stirred for 30 minutes. The reaction mixture is then allowed to warm up to ambient temperature, the solvent is removed on a rotary evaporator and the residue is suspended in diethyl ether. After separation of the triethylammonium salt, the filtrate is again evaporated and the oily residue is taken up in 30 ml. acetonitrile. Trimethylamine is passed through the clear solution at 20° C. until saturated and the reaction mixture is then stirred for 96 hours at ambient temperature in a closed vessel. Thereafter, the precipitate is filtered off with suction, washed with acetonitrile and recrystallised from dichloromethane/acetone. Yield 4.48 g. (58% of theory); m.p. 196°-200° C.

The starting material is prepared analogously to the procedure described in Lipids, 22, 947/1987 and the literature cited therein by reacting the sodium salt of 1,3-benzylideneglycerol with decyl bromide in dimethylformamide (chromatography on silica gel with diethyl ether/hexane (1:5 v/v) as elution agent; yellow oil; yield 59% of theory); the 1,3-dioxan obtained is opened with NBS in dichloromethane to give 3-bromo-2-decyloxypropyl benzoate (yellow oil; used in the next reaction as crude product) and this is reacted with the sodium salt of dodecylmercaptan in ethanol (chromatography on silica gel with diethyl ether/hexane (1:5 v/v) as elution agent; yellow oil; yield 78% of theory).

EXAMPLE 2

3-Decylmercapto-2-dodecyloxypropyl-1-phosphoric acid monocholine ester

This is prepared analogously to Example 1. Yield 44% of theory; m.p. 195° C.

The 3-decylmercapto-2-dodecyloxypropan-1-ol used as starting material is prepared in the manner described in Example 1 (colourless oil; yield 61% of theory).

EXAMPLE 3

3-Decylmercapto-2-decyloxypropyl-1-phosphoric acid monocholine ester

This is prepared analogously to Example 1. Yield 37% of theory; wax-like consistency.

The 3-decylmercapto-2-decyloxypropan-1-ol used as starting material is prepared in the manner described in Example 1 (yellowish oil; yield 47% of theory).

EXAMPLE 4

3-Dodecylmercapto-2-dodecyloxypropyl-1-phosphoric acid monocholine ester

This is prepared analogously to Example 1. Yield 61% of theory; m.p. 230° C. (decomp.).

The 3-dodecylmercapto-2-dodecyloxypropan-1-ol used as starting material is prepared analogously to the process described in Example 1 (yellowish oil; yield 42% of theory).

EXAMPLE 5

3-Hexadecylmercapto-2-decyloxypropyl-1-phosphoric acid monocholine ester

This is prepared analogously to Example 1. Yield 47% of theory; m.p. 192° C.

The 3-hexadecylmercapto-2-decyloxypropan-1-ol used as starting material is prepared analogously to the process described in Example 1 (yellowish oil; yield 57% of theory).

EXAMPLE 6

3-Decylmercapto-2-hexadecyloxypropyl-1-phosphoric acid monocholine ester

This is prepared analogously to Example 1. Yield 59% of theory; m.p. 232° C. (decomp.).

The 3-decylmercapto-2-hexadecyloxypropan-1-ol used as starting material is prepared as described in Example 1 (yellow oil; yield 55% of theory).

EXAMPLE 7

3-Hexadecylmercapto-2-hexadecyloxypropyl-1-phosphoric acid monocholine ester

This is prepared analogously to Example 1. Yield 59%; m.p. 233° C. (decomp.).

This compound has already been described but prepared by a different synthesis route (see Gazz. Chim. Ital., 116, 25/1986).

The 3-hexadecylmercapto-2-hexadecyloxypropan-1-ol used as starting material is prepared as described in Example 1 (yellowish oil; yield 47% of theory).

EXAMPLE 8

3-Dodecylsulphonyl-2-decyloxypropyl-1-phosphoric acid monocholine ester 1 g. Dodecylmercapto-2-decyloxypropyl-1-phosphoric acid monocholine ester (see Example 1) is dissolved in 10 ml. glacial acetic acid, mixed with 1.8 ml. 30% hydrogen peroxide and stirred at 50° C. for 20 hours. Thereafter, the solvent is removed on a rotary evaporator, the residue is mixed with water, again evaporated and the residue mixed with acetone. After standing overnight in a refrigerator, the crystals obtained are filtered off with suction, washed with acetone and diethyl ether and dried. Yield 750 mg. (71% of theory); m.p. 223°-230° C.

EXAMPLE 9

3-Decylsulphonyl-2-dodecyloxypropyl-1-phosphoric acid monocholine ester

This is prepared analogously to Example 8 from 3-decylmercapto-2-dodecyloxypropyl-1-phosphoric acid monocholine ester (see Example 2). Yield 66% of theory; m.p. 223°-227° C.

EXAMPLE 10

3-Undecylmercapto-2-undecyloxypropyl-1-phosphoric acid monocholine ester

This is prepared analogously to Example 1. Yield 71% of theory; m.p. 230°-233° C. (decomp.).

The 3-undecylmercapto-2-undecyloxypropan-1-ol used as starting material is also prepared as described in Example 1 (oil; yield 49% of theory).

EXAMPLE 11

3-Undecylmercapto-2-decyloxypropyl-1-phosphoric acid monocholine ester

This is prepared analogously to Example 10. Yield 64% of theory; m.p. 227°-231° C. (decomp.).

EXAMPLE 12

3-Tridecylmercapto-2-decyloxypropyl-1-phosphoric acid monocholine ester

This is prepared analogously to Example 10. Yield 55%; m.p. 229°-232° C. (decomp.).

EXAMPLE 13

3-Tetradecylmercapto-2-decyloxypropyl-1-phosphoric acid monocholine ester

This is prepared analogously to Example 10. Yield 63% of theory; m.p. 209°-214° C.

EXAMPLE 14

3-Pentadecylmercapto-2-decyloxypropyl-1-phosphoric acid monocholine ester

This is prepared analogously to Example 10. Yield 31% of theory; m.p. 185° C.

EXAMPLE 15

3-Octylmercapto-2-decyloxypropyl-1-phosphoric acid monocholine ester

This is prepared analogously to Example 10. Yield 45% of theory; m.p. 223°-228° C.

EXAMPLE 16

3-Decylmercapto-2-octyloxypropyl-1-phosphoric acid monocholine ester

This is prepared analogously to Example 10. Yield 35% of theory; m.p. 221°-225° C.

EXAMPLE 17

3-Dodecylmercapto-2-octyloxypropyl-1-phosphoric acid monocholine ester

This is prepared analogously to Example 10. Yield 43% of theory; m.p. 198°-206° C.

EXAMPLE 18

3-Dodecylmercapto-2-methoxypropyl-1-phosphoric acid monocholine ester

This is prepared analogously to Example 10. Yield 39% of theory; m.p. >270° C. (decomp.).

EXAMPLE 19

2,3-Bis-(undecylmercapto)-propyl-1-phosphoric acid monocholine ester

This is prepared analogously to Example 10. Yield 62% of theory; m.p. 197°-205° C.

The starting compound, 2,3-bis-(undecylmercapto)-propan-1-ol, is obtained by reacting 2,3-dibromopropan-1-ol with the sodium salt of undecyl mercaptan in dimethylformamide; yield 61% of theory in the form of an oil.

EXAMPLE 20

1,3-Bis-(dodecylmercapto)-propyl-1-phosphoric acid monocholine ester

This is prepared analogously to Example 10. Yield 26% of theory; m.p. 208°-212° C.

The starting compound, 1,3-bis-(dodecylmercapto)-propan-2-ol, is obtained by reacting 1,3-dibromopropan-2-ol with the sodium salt of dodecyl mercaptan in dimethylformamide; yield 67% of theory in the form of an oil.

EXAMPLE 21

3-Dodecylmercapto-2-decylcarbonylaminopropyl-1-phosphoric acid monocholine ester a) 3-Dodecylmercapto-2-aminopropionic acid 16.5 g. (0.42 mole) solid sodium hydroxide are dissolved in 1600 ml. ethanol, mixed with a solution of 25 g. (0.21 mole) D,L-cysteine in 150 ml. ethanol and, after the dropwise addition of 60 ml. (0.25 mole) dodecyl bromide, stirred for 24 hours at ambient temperature. The precipitate is then filtered off with suction, washed with ethanol and dissolved in water. After acidification with 4N hydrochloric acid, the precipitate is filtered off after 2 hours at 5° C. Yield 48.2 g. (81% of theory); m.p. 215°-218° C. (decomp.).

b) Ethyl 3-dodecylmercapto-2-aminopropionate

The free acid obtained in a) is suspended in 1 liter of ethanol and heated under reflux for 4 hours with the gentle passing in of hydrogen chloride. After cooling, the solvent is removed and the hydrochloride obtained is crystallised from diethyl ether/isohexane. Yield 48.5 g. (84% of theory); m.p. 103°-106° C.

c) Ethyl 3-dodecylmercapto-2-decylcarbonylaminopropionate 8.7 g. (24.6 mole) of the hydrochloride obtained in b) are suspended in a mixture of 90 ml. dichloromethane and 10.5 ml. triethylamine and slowly mixed at ambient temperature with 5.6 g. (27.4 mole) undecanoyl chloride in 50 ml. dichloromethane. The suspension is stirred overnight, mixed with 200 ml. of a saturated aqueous solution of ammonium chloride and the organic phase is washed out with water, dried and evaporated. The residue is used in the next step of the reaction without purification.

d)

3-Dodecylmercapto-2-decylcarbonylaminopropan-1-ol

The crude product obtained in c) in 25 ml. tetrahydrofuran is added dropwise at ambient temperature to a suspension of 0.9 g. lithium borohydride in 25 ml. tetrahydrofuran and then stirred for 3 hours. Hydrolysis is then carried out by the careful addition of 50 ml. of a saturated aqueous solution of ammonium chloride and diluted with 100 ml. diethyl ether. After shaking up, the organic phase is separated off, dried and evaporated. The residue is purified by chromatography on silica gel with diethyl ether/isohexane as elution agent. Yield 8.9 g. (81% of theory, referred to the ethyl 3-dodecylmercapto-2-aminopropionate used); m.p. 64°-67° C.

e)

3-Dodecylmercapto-2-decylcarbonylaminopropane-1-phosphoric acid monocholine ester This is prepared analogously to Example 1. Yield 67% of theory; m.p. 191°-194° C.

EXAMPLE 22

3-Dodecylsulphinyl-2-decyloxypropyl-1-phosphoric acid monocholine ester 1 g. 3-Dodecylmercapto-2-decyloxypropyl-1-phosphoric acid monocholine ester (see Example 1) is dissolved in 8 ml. glacial acetic acid, mixed with 0.2 ml. 30% hydrogen peroxide and stirred for 3 days at ambient temperature. Thereafter, the reaction mixture is evaporated on a rotary evaporator and the residue is crystallised from acetone. Yield 0.65 g. (63% of theory); m.p. 230°-233° C. (decomp.).

EXAMPLE 23

3-Tetradecylsulphinyl-2-decyloxypropyl-1-phosphoric acid monocholine ester

This is prepared analogously to Example 22 from the 3-tetradecylmercapto derivative (see Example 13) in a yield of 71% of theory; m.p. 225°-230° C.

EXAMPLE 24

3-Undecylsulphinyl-2-undecyloxypropyl-1-phosphoric acid monocholine ester

This is prepared analogously to Example 22 from the 3-undecylmercapto derivative (see Example 10) in a yield of 61% of theory; m.p. 232°-235° C. (decomp.).

EXAMPLE 25

3-Tridecylsulphinyl-2-decyloxypropyl-1-phosphoric acid monocholine ester

This is prepared analogously to Example 22 from the 3-tridecylmercapto derivative (see Example 12) in a yield of 68% of theory; m.p. 232°-234° C. (decomp.).

EXAMPLE 26

3-Decylsulphinyl-2-dodecyloxypropyl-1-phosphoric acid monocholine ester

This is prepared analogously to Example 22 from the 3-decylmercapto derivative (see Example 2) in a yield of 61% of theory; m.p. >226° C. (decomp.).

EXAMPLE 27

3-Undecylmercapto-2-decyloxymethylpropyl-1-phosphoric acid monocholine ester

This is prepared analogously to the procedure described in Lipids, 22, 947/1987, in which 5-decyloxymethyl-2-phenyl-1,3-dioxan is obtained by the reaction of the 5-hydroxymethyl derivative with sodium hydride in dimethylformamide, followed by reaction with decyl bromide, the yield being 73% of theory. Yield 49% of theory; m.p. 317°-220° C. (decomp.).

EXAMPLE 28

1-Dodecylmercapto-3-decyloxypropyl-2-phosphoric acid monocholine ester a) 1-Decyloxy-2,3-epoxypropane 4.23 ml. (0.05 mole) epibromohydrin in a two-phase mixture of 150 ml. dichloromethane, 150 ml. 50% aqueous sodium hydroxide solution and 3.4 g. tetrabutylammonium hydrogen sulphate are mixed at ambient temperature with 9.52 ml. (0.05 mole) decan-1-ol and stirred overnight. The reaction mixture is then diluted with water and the organic phase is separated off, washed with water and evaporated. The oily residue is purified by column chromatography on silica gel with diethyl ether/isohexane (1:15 v/v). Yield 5.0 g. (47% of theory).

b) 1-Dodecylmercapto-3-decyloxypropan-2-ol 1.6 g. (7.5 mmole) of the epoxide from a) in 16 ml. ethanol is mixed at ambient temperature with 2.3 ml. (9.6 mmole) dodecyl mercaptan and 0.2 g. pulverised potassium hydroxide and stirred overnight. Thereafter, the reaction mixture is diluted with water and extracted with dichloromethane and the organic phase is washed with water, dried and evaporated. The residue is purified by column chromatography on silica gel 60 with diethyl ether/isohexane (1:5 v/v). Yield 2.4 g. (76% of theory) in the form of a colourless oil.

c) 1-Dodecylmercapto-3-decyloxypropyl-2-phosphoric acid monocholine ester

This is prepared analogously to Example 1. Yield 54% of theory; m.p. 219°-224° C.

EXAMPLE 29

The inventive compounds possess an antiviral activity and can therefore be used in the treatment of HIV-related diseases or infections. In order to prove the anti-HIV-activity in cell and tissue cultures, the direct inhibition of the HIV replication was determined in cells.

HIV infected human T-lymphoma cells or human fetal lung cells were treated with the inventive compound by using different concentration ranges of the test compound. The amount of the viruses was then determined by way of new infection of human fetal lung cells. The decrease of the resulting positive HIV-infected cells was regarded as a measure for the antiviral activity of the compound tested.

The following table gives the corresponding concentration, which results in an inhibition of the replication of 50% ($IC_{50}$-value):

TABLE:

Tab: $IC_{50}$-values for some representative compounds

| Compound (example) | $IC_{50}$-value ($\mu g/ml$) |
|---|---|
| 4 | 4 |
| 5 | 20 |
| 6 | 50 |
| 8 | 2 |
| 9 | 2 |
| 11 | 20 |
| 13 | 4 |
| 20 | 4 |
| 21 | 5 |
| 22 | 4 |
| 24 | 4 |
| 25 | 2 |

This shows the efficacy of the compounds in reducing the infectivity of the virus.

It will be understood that the specification and examples are illustrative but not limitative of the present invention and that other embodiments within the spirit and scope of the invention will suggest themselves to those skilled in the art.

We claim:

1. Method for inhibiting the multiplication of human immunodeficiency virus in an infected subject which comprises administering to said subject a compound of the formula

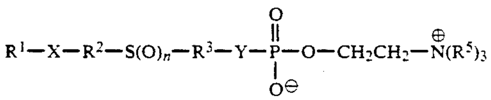

wherein $R^1$—X—$R^2$ is a straight-chain saturated aliphatic hydrocarbon moiety having from 10 to 20 carbon atoms, $R^3$ is

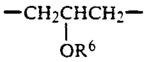
or
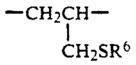

in which $R^6$ is a straight-chain saturated aliphatic hydrocarbon moiety having from 10 to 15 carbon atoms, $R^5$ is a hydrogen atom, a methyl group, or an ethyl group, and y is an oxygen atom, n is 0, 1 or 2, including the optical isomers thereof and the pharmacologically acceptable salts thereof, in sufficient amount to inhibit multiplication of said virus.

2. Method of claim 1, wherein said compound is administered in an amount ranging from about 0.1 to about 100 mg per day per kilogram of body weight.

3. Method of claim 2, wherein said compound is administered in an amount ranging from about 0.2 to about 80 mg per day per kilogram of body weight.

4. Method of claim 1, wherein said compound is administered from 1 to 5 times per day.

5. Method of claim 1, wherein said compound is selected from the group consisting of:

3-dodecylmercapto-2-decyloxypropyl-1-phosphoric acid monocholine ester, 3-decylmercapto-2-hexadecyloxypropyl-1-phosphoric acid monocholine ester, 3-dodecylsulphonyl-2-decyloxypropyl-1-phosphoric acid monocholine ester, 3-decylsulphonyl-2-dodecyloxypropyl-1-phosphoric acid monocholine ester, 3-undecylmercapto-2-decyloxypropyl-1-phosphoric acid monocholine ester, 3-tetradecylmercapto-2-decyloxypropyl-1-phosphoric acid monocholine ester, 1,3-bis-(dodecylmercapto)-propyl-2-phosphoric acid monocholine ester, 3-dodecylsulphinyl-2-decyloxypropyl-1-phosphoric acid monocholine ester, 3-undecylsulphinyl-2-undecyloxypropyl-1-phosphoric acid monocholine ester, 3-tridecylsulphinyl-2-decyloxypropyl-1-phosphoric acid monocholine ester, 3-dodecylmercapto-2-dodecyloxy propyl-1-phosphoric acid monocholine ether, 3-decylmercapto-2-dodecyloxypropyl-1-phosphoric acid monocholine ester, 3-undecylmercapto-2-undecyloxypropyl-1-phosphoric acid monocholine ester, and 3-decylsulphinyl-2-dodecyloxypropyl-1-phosphoric acid monocholine ester.

6. Method of claim 5 in which the compound is 3-dodecylmercapto-2-decyloxypropyl-1-phosphoric acid monocholine ester.

7. Method of claim 5 in which the compound is 3-decylmercapto-2-dodecyloxypropyl-1-phosphoric acid monocholine ester.

8. Method of claim 5 in which the compound is 3-undecylmercapto-2-undecyloxypropyl-1-phosphoric acid monocholine ester.

* * * * *